United States Patent [19]

Radimerski et al.

[11] 4,183,868

[45] Jan. 15, 1980

[54] PROCESS FOR THE PREPARATION OF 2,6-DIALKYL-N-ALKYLANILINES

[75] Inventors: Paul Radimerski, Oberwil; Milos Rusek, Binningen, both of Switzerland

[73] Assignee: Ciba-Geigy Corporation, Ardsley, N.Y.

[21] Appl. No.: 899,903

[22] Filed: Apr. 26, 1978

[51] Int. Cl.$^2$ .......................... C07C 85/06; B01J 23/64
[52] U.S. Cl. .................................... 260/573; 252/470; 260/577
[58] Field of Search ................. 260/577, 573; 252/470

[56] References Cited

U.S. PATENT DOCUMENTS

| | | | |
|---|---|---|---|
| 2,031,475 | 2/1936 | Frazer | 252/467 X |
| 2,416,901 | 3/1947 | Carmody | 252/470 X |
| 2,864,873 | 12/1958 | Miller et al. | 252/470 X |
| 3,819,709 | 6/1974 | Murai et al. | 260/577 |
| 3,904,553 | 9/1975 | Campbell et al. | 252/470 X |
| 3,929,681 | 12/1975 | Buonomo et al. | 252/470 X |
| 3,937,730 | 2/1976 | Vogel et al. | 260/562 B |
| 3,952,056 | 4/1976 | Vogel et al. | 260/562 B |
| 3,956,459 | 5/1976 | Whitman et al. | 423/213.5 |
| 4,082,802 | 4/1978 | Nakagawa et al. | 260/577 X |

FOREIGN PATENT DOCUMENTS

| | | | |
|---|---|---|---|
| 2061709 | 7/1971 | Fed. Rep. of Germany | 260/577 |
| 2305495 | 10/1976 | Fed. Rep. of Germany | 260/573 |
| 2328340 | 4/1978 | Fed. Rep. of Germany | 260/573 |
| 48-85511 | 11/1973 | Japan | 260/577 |
| 50-22542 | 7/1975 | Japan | 260/577 |

OTHER PUBLICATIONS

Kirk–Othmer Encyclopedia of Chemical Technology, vol. 2, pp. 411–413 & 425–426.
Corson et al., "J. Org. Chem.", vol. 21, p. 474 (1956).
Rice et al., "JACS", vol. 77, 4052–4054 (1955).
Nakagawa et al., "Chem. AB.", vol. 79, AB. No. 136769w (1973).

*Primary Examiner*—John Doll
*Attorney, Agent, or Firm*—Frederick H. Rabin

[57] ABSTRACT

A process for the preparation of 2,6-dialkyl-N-alkylanilines is disclosed, which process comprises the reaction of a 2,6-dialkylaniline with an alkanol at 200° to 350° C. in the presence of a copper-containing catalyst which contains 0.05 to 10% by weight of palladium or platinum.

9 Claims, No Drawings

PROCESS FOR THE PREPARATION OF 2,6-DIALKYL-N-ALKYLANILINES

The present invention relates to a process for the preparation of 2,6-dialkyl-N-alkylanilines of the formula I

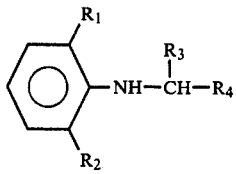

in which $R_1$ and $R_2$ independently of one another are each methyl or ethyl, $R_3$ is hydrogen, methyl or ethyl and $R_4$ is an alkyl group having 1 to 11 carbon atoms or an alkoxymethyl group having 1 to 8 carbon atoms in the alkyl group.

The present invention relates in particular to a process for the preparation of 2,6-dialkyl-N-alkylanilines of the formula I in which $R_1$ and $R_2$ independently of one another are each methyl or ethyl, $R_3$ is hydrogen or methyl and $R_4$ is alkoxymethyl having 1 to 3 carbon atoms in the alkyl group.

2,6-Dialkyl-N-alkylanilines of the formula I are valuable intermediates for the preparation of pesticidal active compounds. Thus, 2,6-dialkyl-N-alkylanilines of the formula I can be converted by means of halogenoacetyl halides, such as chloroacetyl chloride or bromoacetyl bromide, into the corresponding acetanilides having a pesticidal action. Acetanilides of this type and their preparation and use are described, for example, in U.S. patent application Ser. No. 328,202 filed on Jan. 31, 1973, in U.S. Pat. Nos. 3,952,056 and 3,937,730 and also in German Pat. No. 2,305,495 and German Auslegeschrift No. 2,328,340.

It is known to prepare N-alkylanilines by reacting anilines with alkyl halides, alkyl tosylates or alkyl phosphates. When this method is used, however, considerable amounts of N,N-dialkylanilines are always formed in addition to the desired N-monoalkylanilines. Therefore, because its selectivity is too low, this process is unsuitable for industrial preparation of compounds of the formula I. Moreover, this process presents ecological problems since the waste waters always contain large amounts of hydrogen halide, toluenesulphonic acid or phosphoric acid, or salts of these acids.

It is also known to prepare anilines by reaction with carbonyl compounds in the presence of hydrogen and hydrogen transfer catalysts. The essential disadvantage of this process is that, because the selectivity is too low, considerable amounts of undesired by-products, such as N,N-dialkylaniline and condensation products, are formed, which impair the yield of the desired N-monoalkylaniline.

It has also already been proposed to react anilines in the presence of catalysts with alcohols to give N-alkylanilines (cf. Kirk-Othmer, Encyclopaedia of Chemical Technology, 2nd edition, volume 2, 412–13). Catalysts used in this process were, in addition to aluminium oxide, aluminium silicate, a mixture of phosphoric acid and bentonite, and mineral acids, such as hydrochloric acid or sulphuric acid, also hydrogen transfer catalysts. For example, according to a process described in U.S. Pat. No. 2,580,284, aniline is reacted, in the presence of a copper-containing alumina catalyst and in the presence of hydrogen, with methanol to give N-methylaniline in a yield of 96% of theory. Furthermore, ethanol can be reacted in the presence of Raney nickel to give N-ethylaniline in a yield of 80 to 83% of theory. (cf. J. Org. Chem. 21, 474- (1956) and J. Amer. Chem. Soc. 77, 4052–4054 (1955)). When aniline and methanol are reacted in the presence of copper chromite and hydrogen, N-methylaniline is formed in virtually quantitative yield as the sole reaction (cf. Japanese Published Specification No. 73/49,727; C.A. 79, (1973) 136,769w and German Published Specification No. 2,061,709).

As the above discussion of the state of the art shows, the reaction of aniline with alcohols in the presence of hydrogen and hydrogen transfer catalysts results in N-alkylanilines in excellent yields. However, it is not possible by this process to react 2,6-dialkylanilines with alcohols, and especially with alkoxyalkanols, to give the corresponding 2,6-dialkyl-N-alkylanilines.

The object on which the present invention is based is, therefore, to provide a process by which 2,6-dialkylanilines can be reacted with alcohols to give the corresponding 2,6-dialkyl-N-alkylanilines in good yields.

It has now been found that 2,6-dialkyl-N-alkylanilines of the formula I can be prepared in excellent yield by reacting a 2,6-dialkylaniline of the formula II

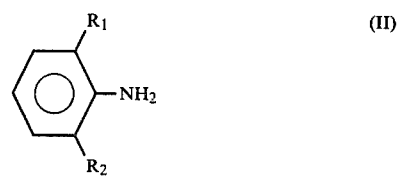

in which $R_1$ and $R_2$ are as defined under formula I, in the presence of a copper-containing catalyst which contains 0.05 to 10% by weight of palladium or platinum, at 200° to 350° C., with an alcohol of the formula III

in which $R_3$ and $R_4$ are as defined under formula I.

The copper-containing catalysts are generally commercially available catalysts which contain copper, for example copper oxide or mixtures of copper oxide with other metal oxides, such as chromium oxide or zinc oxide. The catalysts can also be precipitated on an inert carrier, such as silica gel, aluminium oxide or silicates, for example magnesium silicate, and contain, as further additives, small amounts of alkaline earth metal oxides or alkali metal oxides, such as barium oxide or sodium oxide.

Copper oxide/chromium oxide catalysts which have a molar ratio of copper oxide to chromium oxide of 1:1 to 15:1 and which contain 0.05 to 10% by weight, preferably 0.2 to 3% by weight, of palladium or platinum are particularly suitable. Catalysts of this type are novel.

The catalysts to be used according to the invention can be prepared by saturating a commercially available copper-containing catalyst of the abovementioned type with a solution of a platinum salt or palladium salt, for example platinum acetate or palladium acetate, and then drying the catalyst. It is, however, also possible to prepare the catalysts to be used according to the invention simply by mixing a commercially available copper-containing catalyst of the above-mentioned type with a solid substance containing platinum or palladium, for example platinum oxide, platinum-on-charcoal, palladium acetate, palladium hydroxide-on-barium sulphate and the like.

A particularly suitable catalyst to be used according to the invention is obtained when a mixture of copper hydroxycarbonate and hydrated chromium oxide is first precipitated from an aqueous solution containing approximately equimolar amounts of a copper-II salt and a chromium-III salt, by adding an aqueous solution of an alkali metal carbonate, for example potassium carbonate solution, the precipitation mixture is freed from alkali metal ions by washing with water and the mixture obtained by filtering off the bulk of the water with suction is extruded, dried and saturated with a solution of a palladium salt or platinum salt and dried again. For example, the extruded catalyst particles can be saturated with a solution of palladium acetate in benzene. However, the preparation of the catalyst can also be carried out by dissolving a corresponding amount of a platinum salt or palladium salt together with the copper-II salt and the chromium-III salt in water and precipitating the platinum or palladium, together with copper and chromium, in the form of the basic carbonate by adding a solution of an alkali metal carbonate. By extruding and drying the precipitated carbonates, the ready-to-use catalyst is thus obtained direct. Suitable copper-II salts and chromium-III salts are, for example, the chlorides, sulphates and acetates and especially the nitrates.

Before it is used according to the invention, the catalyst is activated with hydrogen. This activation is effected by passing hydrogen or a mixture of hydrogen and nitrogen over the catalyst at temperatures of between 120° and 350° C. The subsequent reaction of a 2,6-dialkylaniline of the formula II with an alcohol of the formula III is preferably carried out at a temperature of between 220° and 300° C. The process according to the invention is carried out under normal pressure or under an excess pressure of up to 50 bars. Particularly advantageous results are obtained in the pressure range of 2 to 5 bars.

According to the invention, the molar ratio of the 2,6-dialkylaniline of the formula II to the alkanol of the formula III is 1:1 to 1:3, preferably 1:1.5 to 1:2.5.

It is advantageous to carry out the N-alkylation of a 2,6-dialkylaniline of the formula II with an alkanol of the formula III in the presence of hydrogen. The amount of hydrogen depends, on the one hand, on the boiling point of the components present in the reaction mixture and, on the other hand, on the pressure under which the process is carried out. Under normal pressure, the reaction is advantageously carried out in the presence of 1 to 3 mols of hydrogen per mol of 2,6-dialkylaniline of the formula II. In the preferred pressure range of 2 to 5 bars, 2 to 10 mols of hydrogen per mol of 2,6-dialkylaniline of the formula II are advantageously employed. At higher pressures even greater amounts of hydrogen can be employed, especially when high-boiling reaction products form.

By means of the process according to the invention it becomes possible for even 2,6-dialkylanilines, which hitherto were not accessible to alkylation with alcohols, to be alkylated with alcohols. As a result, the intermediates of the formula I can be prepared, with high conversion and excellent selectivity, using inexpensive, readily accessible alcohols as the starting materials. Because of the short reaction times, the process can easily be carried out continuously and is therefore very suitable for an industrial preparation of intermediates of the formula I. Compared with those processes in which the alkylation is carried out with alkyl halides or alkyl tosylates, the process also offers substantial advantages from an ecological point of view, since the high loading of the waste water with salts, which arises in the case of the former processes, does not occur.

The process according to the invention is illustrated in more detail by the examples which follow.

EXAMPLE 1

Preparation of 2,6-dimethyl-N-(2'-methoxyethyl)-aniline

A commercially available catalyst (Cu-0203 T 1/8), which contains 78% by weight of copper oxide and 20% by weight of chromium oxide and is produced by Harshaw Chemie N.V., de Meern, Holland, is comminuted to a particle size of 0.5 to 0.8 mm, saturated with a solution of palladium acetate and dried in a vacuum drying cabinet at 50° to 120° C. The catalyst prepared in this way contains 0.2% by weight of palladium.

In a quartz tube 30 cm in length and 0.5 cm in diameter, which is arranged vertically and surrounded by a heating jacket, 2 ml of this catalyst are activated at 130° C., in the manner described in Example 2, and then heated to 275° C. under hydrogen. At 275° C., 1.21 g of 2,6-dimethylaniline, 1.52 g of 2-methoxyethanol and 0.67 Nl of hydrogen are then passed, per hour, under normal pressure, through the reactor from top to bottom. The mixture which issues from the reactor is condensed and worked up by distillation.

For a test period of 72 hours, the following results are obtained:
total conversion, based on 2,6-dimethylaniline: 69.4%
selectivity, based on 2,6-dimethylaniline: 80.8%
conversion to 2,6-dimethyl-N-(2'-methoxyethyl)-aniline: 56.0%
conversion to the N-ethylated product: 6.2%
conversion to the N,N-dialkylated product: 0.8%

EXAMPLE 2

Preparation of 2,6-dimethyl-N-(2'-methoxyethyl)-aniline

In a steel tube reactor 110 cm in length and 2 cm in diameter, which is arranged vertically, 100 ml of a copper oxide/chromium oxide catalyst (molar ratio $CuO:Cr_2O_3 = 12:1$), which contains 1.5% by weight of palladium, is heated to 130° C. in a stream of nitrogen and activated with a nitrogen/hydrogen mixture which initially contains 2% by volume of hydrogen. During the activation, the proportion of hydrogen in the nitrogen/hydrogen mixture is continuously increased until, finally, pure hydrogen is passed over the catalyst. The temperature of the catalyst in the stream of hydrogen is then raised to 275° C., and subsequently 60.6 g (0.5 mol) of 2,6-dimethylaniline, 76 g (b 1 mol) of 2-methoxyethanol and 112 Nl (5 mols) of hydrogen are passed per hour, under an excess pressure of 5 bars, through the reactor from top to bottom. The reaction mixture which issues from the lower end of the reactor is condensed and worked up by distillation. After a start-up phase, the following results are obtained:
total conversion, based on 2,6-dimethylaniline: 79.3% selectivity, based on 2,6-dimethylaniline: 92.4%
total conversion, based on 2-methoxyethanol: 41%
selectivity, based on 2-methoxyethanol: 90.6%
conversion to 2,6-dimethyl-N-(2'-methoxyethyl)-aniline: 73.3%
conversion to the N-ethylated product: 4.4%
conversion to the N,N-dialkylated product: 0.1%

EXAMPLE 3

Preparation of 2,6-dimethyl-N-(2'-methoxyethyl)-aniline

In an adiabatic reactor, 100 ml of a copper oxide/chromium oxide catalyst (molar ratio $CuO:Cr_2O_3 = 2:1$) containing 1.5% by weight of palladium are activated in the manner described in Example 2 and heated in the stream of hydrogen to 275° C. 60.6 g (0.5 mol) of 2,6-dimethylaniline, 76 g (1.0 mol) of 2-methoxyethanol and 67.2 Nl (3mols) of hydrogen are then passed, at 275° C. and under a pressure of 4 bars (absolute), through the catalyst bed. The reaction mixture which issues from the reactor is condensed and worked up by distillation.

After the stationary state has been reached, the following results are obtained:
total conversion, based on 2,6-dimethylaniline: 81.5%
selectivity, based on 2,6-dimethylaniline: 92.2%
total conversion, based on 2-methoxyethanol: 42.3%
selectivity, based on 2-methoxyethanol: 88.7%
conversion to 2,6-dimethyl-N-(2'-methoxyethyl)-aniline: 75.1%
conversion to the N-ethylated product: 5.2%
conversion to the N,N-dialkylated product: 0.15%

EXAMPLE 4

In a Pyrex glass tube, which is arranged vertically and provided with a heating jacket, a mixed catalyst consisting of 74% by weight of platinum-on-charcoal (1% by weight of Pt) and 26% by weight of a copper oxide/chromium oxide catalyst which contains 78% by weight of copper oxide and 20% by weight of chromium oxide (Harschaw Cu-0203 T) is activated at 200° C., first with a nitrogen/hydrogen mixture and then with pure hydrogen. Per g of catalyst and per hour, 0.35 g of a mixture of 53% by weight of 2-ethyl-6-methylaniline and 47% by weight of isopropanol (molar ratio of 2-ethyl-6-methylaniline to isopropanol=1:2) and, at the same time, 67.2 Nl (3 mols) of hydrogen per mol of 2-ethyl-6-methylaniline are passed under normal pressure over the catalyst heated to 220° C. in the stream of hydrogen.

Examination, by gas chromatography, of the reaction mixture issuing from the reactor gives a total conversion of 2-ethyl-6-methylaniline of 30% and a yield of 2-ethyl-6-methyl-N-isopropylaniline of 95% of theory, based on the 2-ethyl-6-methylaniline converted.

EXAMPLE 5

Preparation of 2,6-dimethyl-N-n-octyl-aniline (a) Preparation of the catalyst

A solution of 2.6 kg of potassium carbonate in 20 l of deionised water is added to a stirred solution of 1.6 kg of copper-II nitrate trihydrate and 2.6 kg of chromium-III nitrate nonahydrate in 26 l of deionised water at room temperature, and a suspension with a pH of about 7.5 forms. After the addition of the potassium carbonate solution has ended, the resulting suspension is stirred for 30 minutes. The precipitate is then allowed to settle out and the mother liquor is drawn off. The residue is suspended in 30 l of deionised water. The precipitate is then allowed to settle out again and the wash water is drawn off. This washing operation is repeated until no further nitrate can be detected by the "Merckoquant" nitrate test (catalogue No. 10,020). The consumption of water is about 500 l and the nitrate concentration after washing is less than 10 ppm.

The precipitate is then filtered off with suction on a Buchner funnel and sucked dry, giving a filter cake with a water content of about 90% by weight. The filter cake, which is obtained in the form of a paste, is then extruded and the extrudate is dried for 16 hours in a vacuum drying cabinet at 160° C. After drying, the extruded strands are broken into small pieces.

A solution of 3.55 g of palladium acetate in 600 ml of benzene is then added to 200 g (1 l) of the dried extrudate. The mixture is transferred to a rotary evaporator and the benzene is evaporated off at a maximum temperature of 50° C. and under a pressure of 300 mm Hg. After removing the benzene, the catalyst is dried in a vacuum drying cabinet under a pressure of 20 mm Hg and at a temperature of 50° C. for 2 hours. The temperature is then raised to 120° C. in the course of 4 to 6 hours and the catalyst is dried for a further half hour at 120° C. A copper chromide catalyst which contains about 0.8% by weight of palladium is obtained in this way.

(b) Preparation of 2,6-dimethyl-N-n-octyl-aniline

In a Pyrex glass tube which is arranged vertically and provided with a heating jacket, the catalyst prepared by the above method (a) is first heated to 250° C. in a stream of nitrogen and then activated for 16 hours with a nitrogen/hydrogen mixture with a hydrogen content of 3.3% by volume. Per g of catalyst and per hour, 1.8 g of a mixture of 31.7% by weight of 2,6-dimethylaniline and 68.3% by eight of n-octanol (molar ratio of 2,6-dimethylaniline to n-octanol=1:2), and 89.6 Nl(4 mols) of hydrogen per mol of 2,6-dimethylaniline, are then metered in at the top of the reactor, at 270° to 275° C. and under normal pressure.

After the reactor has been in operation for 40 hours, the analyses of the product issuing from the reactor, which are carried out continuously by gas chromatography, show a total conversion of 2,6-dimethylaniline of 63%. The yield of 2,6-dimethyl-N-n-octylaniline is 90% of theory, based on the 2,6-dimethylaniline converted.

EXAMPLE 6

Preparation of 2,6-dimethyl-N-ethyl-aniline

In a Pyrex glass tube, which is arranged vertically and provided with a heating jacket, the catalyst prepared by the method described in Example 5 is activated as described in Example 6. Per g of catalyst and per hour, 1.8 g of a mixture of 56.81% by weight of 2,6-dimethylaniline and 43.19% by weight of ethanol (molar ratio of 2,6-dimethylaniline to ethanol=1:2), and 33.6 Nl (1.5 mols) of hydrogen per mol of 2,6-dimethylaniline, are then passed, at 275° C. and under normal pressure, through the reactor from top to bottom. Analysis, by gas chromatography, of the product issuing from the reactor gives a total conversion of 2,6-dimethylaniline of 66%. The yield of 2,6-dimethyl-N-ethyl-aniline is 96% of theory, based on the 2,6-dimethylaniline converted.

EXAMPLE 7

Preparation of 2,6-dimethyl-N-(2'-propoxyethyl)-aniline

In a steel tube with a diameter of 2.54 cm, which is arranged vertically and provided with a heating jacket, the catalyst prepared according to Example 5(a) is activated with a nitrogen/hydrogen mixture with a hydrogen content of 3.3% by volume for 16 hours at 250° C. The total throughput is 60 ml of the gas mixture per g of catalyst. Per g of catalyst and per hour, 1.0 g of a mixture of 2-propoxyethanol and 2,6-diethylaniline (molar ratio 2:1), together with 56 Nl (2.5 mols) of hydrogen per mol of 2,6-diethylaniline, are then passed over the catalyst at 270° C. and under a pressure of 2 bars. The reaction mixture which issues from the reactor and consists of 2-propoxyethanol, 2,6-diethylaniline, 2,6-diethyl-N-(2'-propoxyethyl)-aniline and by-products is analysed continuously by gas chromatography. The total conversion of 2,6-diethylaniline and the selectivity are calculated from the analytical data. The results are summarised in the table which follows:

| Duration of the experiment (hours) | % total conversion of 2,6-diethylaniline | Selectivity |
|---|---|---|
| 1–72 | 66 | 86.9 |
| 72–160 | 58.9 | 87.3 |
| 160–248 | 56.0 | 89.3 |
| 248–336 | 65.7 | 91.5 |

EXAMPLE 8

Alkylation of various aniline derivatives with 2-methoxyethanol using a copper oxide/chromium oxide catalyst without the addition of platinum or palladium In a Pyrex glass tube reactor, which is arranged vertically and provided with a heating jacket, a commercially available copper oxide/chromium oxide catalyst which contains 78% by weight of copper oxide and 20% by weight of chromium oxide (Harschaw Cu-0203 T) is heated to 200° C. under nitrogen and then activated with a nitrogen/hydrogen mixture which initially contains 3.3% by volume of hydrogen. During the activation, the proportion of hydrogen in the nitrogen/hydrogen mixture is continuously increased until, finally, pure hydrogen is passed over the catalyst. The temperature of the catalyst is then raised to 250° C. in the stream of hydrogen. Per g of catalyst and per hour, 0.73 g (7.84 mmols) of aniline and 1.19 g (15.68 mmols) 2-methoxyethanol are then metered in at the top of the reactor. The reaction mixture which issues from the reactor is condensed and analysed by gas chromatography. The total conversion of aniline and the conversion to N-(2-methoxyethyl)-aniline are calculated on the basis of the analytical data.

Subsequently, without interrupting the experiment, 0.73 g (6.81 mmols) of o-toluidine, in place of aniline, and 1.04 g (13.62 mmols) of 2-methoxyethanol are passed, per g of catalyst and per hour, over the catalyst under the same conditions. The reaction mixture which issues from the reactor is again analysed continuously by gas chromatography during the period of the experiment. The total conversion of o-toluidine and the conversion to N-(2'-methoxyethyl)-o-toluidine are again calculated on the basis of the analytical data.

0.73 g (6.02 mmols) of 2,6-dimethylaniline, in place of o-toluidine, and 0.92 g (12.04 mmols) of 2-methoxyethanol are then passed, per g of catalyst and per hour, over the catalyst under the same conditions and the composition of the reaction mixture which issues from the reactor is analysed by gas chromatography. The total conversion of 2,6-dimethylaniline and the conversion to 2,6-dimethyl-N-(2'-methoxyethyl)-aniline are calculated from the analytical data.

Finally, in order to monitor the activity of the catalyst, 0.73 g (7.84 mmols) of aniline and 1.19 g (15.68 mmols) of 2-methoxyethanol are again passed, per g of catalyst and per hour, over the catalyst, under the same conditions and without interrupting the experiment, and the total conversion of aniline and the conversion to N-(2'-methoxyethyl)-aniline are determined.

The results of the individual experiments are summarised in the table which follows.

| Aromatic amine | Duration of the experiment [hours] | % total conversion of aromatic amine | % conversion to N-(2'-methoxyethyl)-aniline |
|---|---|---|---|
| aniline | 0–21 | 35 | 34 |
| o-toluidine | 21–50 | 31 | 30 |
| 2,6-dimethylaniline | 50–80 | 4 | 3.4 |
| aniline | 80–100 | 33 | 32 |

The experimental results show that it is virtually not possible to carry out the reaction of 2,6-dimethylaniline and 2-methoxyethanol to give N-(2'-methoxyethyl)-2,6-dimethylaniline without the addition, according to the invention, of palladium or platinum.

What is claimed is:

1. A process for the preparation of a 2,6-dialkyl-N-alkylaniline of the formula I

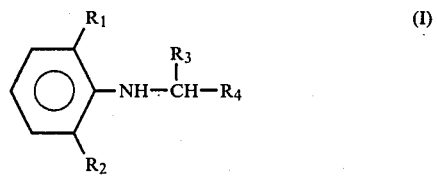

in which $R_1$ and $R_2$ independently of one another are each methyl or ethyl, $R_3$ is hydrogen, methyl or ethyl and $R_4$ is an alkyl group having 1 to 11 carbon atoms or an alkoxymethyl group having 1 to 8 carbon atoms in the alkyl group, which comprises reacting a 2,6-dialkylaniline of the formula II

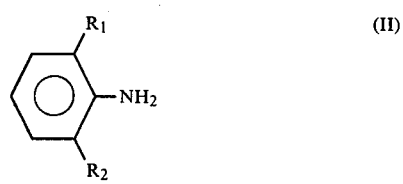

in which $R_1$ and $R_2$ are as defined under formula I, in the presence of a copper-containing catalyst which contains 0.05 to 10% by weight of palladium or platinum, at 200° to 350° C., with an alcohol of the formula III

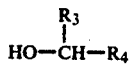

in which $R_3$ and $R_4$ are as defined under formula I.

2. A process according to claim 1, which comprises carrying out the reaction of a 2,6-dialkylaniline of the formula II with an alcohol of the formula III in the presence of hydrogen.

3. A process according to claim 1, which comprises carrying out the reaction of a 2,6-dialkylaniline of the formula II with an alcohol of the formula III at a temperature of between 220° and 300° C.

4. A process according to claim 1, which comprises carrying out the reaction of a 2,6-dialkylaniline of the formula II with an alcohol of the formula III under a pressure of 2 to 5 bars.

5. A process according to claim 1, which comprises carrying out the reaction of a 2,6-dialkylaniline of the formula II with an alcohol of the formula III under normal pressure in the presence of 1 to 3 mols of hydrogen per mol of 2,6-dialkylaniline of the formula II.

6. A process according to claim 1, which comprises carrying out the reaction of a 2,6-dialkylaniline of the formula II with an alcohol of the formula III under a pressure of 2 to 5 bars in the presence of 2 to 10 mols of hydrogen per mol of 2,6-dialkylaniline of the formula II.

7. A process according to claim 1, which comprises carrying out the reaction of a 2,6-dialkylaniline of the formula II with an alcohol of the formula III in the presence of a copper oxide/chromium oxide catalyst which has a molar ratio of copper oxide:chromium oxide of 1:1 to 15:1 and contains 0.05 to 10% by weight, preferably 0.2 to 3% by weight, of palladium or platinum.

8. A catalyst mixture consisting essentially of copper oxide and chromium oxide, wherein the molar ratio of copper oxide to chromium oxide is 1:1 to 15:1, which catalyst mixture additionally contains 0.05 to 10% by weight of palladium or platinum.

9. The catalyst mixture of claim 8 which contains 0.2 to 3% by weight of palladium or platinum.

* * * * *